(12) United States Patent
Haaheim

(10) Patent No.: US 7,361,479 B1
(45) Date of Patent: Apr. 22, 2008

(54) ASSAY

(75) Inventor: Lars Reinhardt Haaheim, Bergen (NO)

(73) Assignee: PlasmAcute AS, Bergen (NO)

( * ) Notice: Subject to any disclaimer, the term of this patent is extended or adjusted under 35 U.S.C. 154(b) by 496 days.

(21) Appl. No.: 10/009,685

(22) PCT Filed: Jun. 14, 2000

(86) PCT No.: PCT/GB00/02316

§ 371 (c)(1),
(2), (4) Date: Apr. 23, 2002

(87) PCT Pub. No.: WO00/77525

PCT Pub. Date: Dec. 21, 2000

(30) Foreign Application Priority Data

Jun. 14, 1999 (GB) .................................. 9913819

(51) Int. Cl.
G01N 33/00 (2006.01)

(52) U.S. Cl. .............................. 435/7.24; 435/2; 435/4; 435/7.1; 435/7.24; 435/7.92; 435/372.2; 435/372.3; 436/507; 436/512; 436/513; 436/518; 436/524; 436/528; 436/17; 436/63; 436/166; 436/175; 436/177; 436/178

(58) Field of Classification Search .................... 435/2, 435/4, 7.21, 7.24, 7.92, 325, 326, 335, 345, 435/372, 372.2, 372.3, 373, 374, 7.1; 436/507, 436/512, 513, 518, 524, 528, 17, 63, 64, 436/166, 175, 176–178

See application file for complete search history.

(56) References Cited

U.S. PATENT DOCUMENTS

| | | | |
|---|---|---|---|
| 4,661,445 A | 4/1987 | Saxinger et al. | 437/435 |
| 5,019,497 A | 5/1991 | Olsson | 435/7.23 |
| 5,188,942 A | 2/1993 | Reddington et al. | 435/28 |
| 5,360,719 A | 11/1994 | Levine et al. | 435/29 |
| 5,637,453 A | 6/1997 | Jehuda-Cohen | 435/5 |

FOREIGN PATENT DOCUMENTS

| | | |
|---|---|---|
| EP | 0 526 952 A3 | 2/1993 |
| EP | WO 96-26443 | 8/1996 |
| EP | 0 822 412 A1 | 2/1998 |
| EP | WO 00-77525 | 12/2000 |

OTHER PUBLICATIONS

Sison A V, Laboratory Methods for early detection of HIV-type-1 in Newborns and Infants, Clinical Microbiology Reviews, 5(3): pp. 238-247 (Jul. 1992).*
Choi, Biosynthesis and Secretion of Immunoglobulins, Immunoglobulins, pp. 345, 346, 348-351 (1981).*
Atkinson et al., Direct Measurement of Antibody Production in Cell Suspensions using ELISA, Journal of Immunological Methods 76: 365-373 (1985).*
Cox et al., Kinetics of early immune response induced after parenteral influenza vaccination (Options for the control of influenza III, 561-571 (1996).*
Atkinson, P., et al.; "Direct measurement of antibody production in cell suspensions using an enzyme-linked immunosorbent assay"; *J. Immunlog. Meth.,* vol. 76, 1985, pp. 365-373.
Czerkinsky, et al., ELISA and other Solid Phase Immunoassays, Ed., D.M. Kenneny and S.J. Challacombe, 1988, Chapter 10, pp. 217-239.
Roitt, I., Brostoff, J., Male, D., "Immunology", 4th Edition, Mosby, London 1996, pp. 6.12-6.13.
Melchers, 1971, Histochemical, J., 3, pp. 389-397.
Amadori et al., "Spontaneous In Vitro Production of Virus-Specific Antibody by Lymphocytes from HIV-Infected Subjects", *Clin,. Immunol. Immunopathol.,* vol. 26, p. 342-351, 1988.
Askonas BA., "Immunoglobulin synthesis and its induction in B-lymphoid cells", *Acta Endocrinol Suppl* (Copenh)., 1975, vol. 194, p. 117-132.
Atkinson et al., "Direct Measurement of Antibody Production in Cell Suspensions Using an Enzyme-Linked Immunosorbent Assay", *J. Immunological Methods,* 1985, vol. 76, p. 365-373.
Buxbaum, J. et al., "Synthesis and assembly of immunoglobulins by malignant human plasmacytes and lymphocytes. II. Heterogeneity of assembly in cells producing IgM proteins", *J. Exp. Med.,* May 1, 1971; vol. 133(5), p. 1118-1130.
Corte, DE, et al., "Biosynthesis of immunoglobulin A (IgA) and immunoglobulin M (IgM). Requirement for J Chain and a disulphide-exchanging enzyme for polymerization", *Biochem J.,* Nov. 1973, vol. 136(3); p. 597-606.
Cox, RJ, et al., "An early humoral immune response in peripheral blood following parenteral inactivated influenza vaccination", *Vaccine,* Aug. 12, 1994(11), p. 993-999.
Cox RJ, et al., "Kinetics of the early immune response induced after parenteral influenza vaccination" in Options for the control of influenza III, 1996, Eds L.E. Brown, A.W. Hampson and R.G. Webster, *Elsevier Science,* p. 561-571.
Ekong T, et al., "Double-staining artefact observed in certain individuals during dual-colour immunophenotyping of lymphocytes by flow cytometry", *Cytometry,* 1993, vol. 14(6), p. 679-684.
el-Madhun AS et al., "Systemic and mucosal immune responses in young children and adults after parenteral influenza vaccination", *J. Infect. Dis.,* Oct. 1998, vol. 178(4), pp. 933-939.

(Continued)

*Primary Examiner*—Gailene R. Gabel
(74) *Attorney, Agent, or Firm*—Morgan, Lewis & Bockius LLP

(57) ABSTRACT

The present invention provides a method of determining the presence or amount of newly synthesized antibody in a sample in response to an immunogen by detecting the released antibodies or parts thereof in a sample containing lymphocytes which have been disrupted whereby to release the synthesized antibodies or parts thereof associated with said lymphocytes whereby to determine the presence or amount of newly synthesized antibody in said sample, methods of diagnosis using said method and kits for performing the method. The method may also be modified to allow detection of non-specific infection indicators.

22 Claims, 5 Drawing Sheets

OTHER PUBLICATIONS

Greene et al., "Modification, optimization and simplification of the spot ELISA technique for the enumeration of cells secreting anti-hapten antibodies", *J. Immunological Methods,* 1990, vol. 129, p. 187-197.

Hetland et al., "The use of flow cytometry to detect the biosynthesis of complement components", *J. Immunological Methods,* 1991, vol. 140, p. 167-171.

Kehrl & Fauci, "Identification, Purification, and Characterization of Antigen-Activated and Antigen-Specific Hunan B Lymphocytes", *J. Exp. Med.,* 1983, vol. 157, p. 1692-1697.

Kelly et al., "The use of the enzyme-linked immunosorbent assay (ELISA) for the detection and quantification of specific antibody from cell cultures", *Immunology,* vol. 37, p. 45-52, 1979.

Quiding et al., "Oral Cholera Vaccination Induces Strong Intestinal Antibody Responses and Interferon-γ Production and Evokes Local Immunological Memory", *J. Clin. Invest.,* 1991, vol. 88, p. 143-148.

Ruedl et al., "A novel and sensitive method for the detection of secreted cell products using time-resolved fluorescence", *J. Immunological Methods,* 1994, vol. 168, p. 61-67.

Sherr CJ et al., "Synthesis and intracellular transport of immunoglobulin in secretory and nonsecretory cells", *Ann. NY Acad Sci.,* Dec. 31, 1971, vol. 190, p. 250-267.

Tartakoff AM et al., "Plasma cell immunoglobulin secretion; arrest is accompanied by alterations of the golgi complex", *J. Exp. Med.,* Nov. 1, 1977, vol. 146(5), p. 1332-1345.

Immunoglobulins in Newly-Born Animals, Biochemistry of Antibodies, pp. 261-262, 1966, author?

Secretion of Immunoglobulins, Immunoglobulins, p. 453, 1981, author?

Yong Sung Choi, Biosynthesis and Secretion of Immunoglobulins, Immunoglobulins, pp. 345-346 and pp. 348-351, 1981.

\* cited by examiner

ASSAY

FIELD OF THE INVENTION

The present invention relates to the detection of antibodies, and in particular to the detection of recently synthesized antibodies produced in response to infection or vaccination etc. in samples, by means of a simple method involving the disruption of lymphocytes prior to detecting the presence of antibody.

BACKGROUND OF THE INVENTION

ELISA has long been used to detect and measure antibody (or antigen) levels. Most commonly, ELISA is used as a serological assay, but it is also used to study the immunochemical properties of antigens or antibodies, and has frequently found application in, for example, the evaluation and characterization of immune responses, to investigate antibody production by cell cultures, and in hybridoma technology.

The ELISA assay is simple to use, sensitive and relatively quick, but it is only able to simply measure the presence of the target antibody in the sample; it cannot distinguish between on-going antibody synthesis in response to the antigen, and antibodies already present from past infection, or by passive transfer. Whilst in some cases, it may suffice simply to obtain information concerning the presence of antibody, it is in other cases desirable to be able to determine whether or not the detected target antibodies are acutely synthesized by the lymphocytes at the time of testing, for example during a vaccination course, or in the diagnosis of infection in infants, to distinguish from passively transferred maternal antibodies. This cannot be achieved in a classical ELISA method.

Other methods have therefore been developed, which enable on-going antibody synthesis to be detected. Particular mention may be made in this regard of the enzyme-linked immunospot (ELISPOT) assay (also known as spot ELISA or ELISA-plaque assay), as reviewed for example by Czerkinsky et al. in ELISA and other Solid Phase Immunoassays, Ed. D. M. Kemeny and S. J. Challacombe, 1988, Chapter 10, 217-239. This technique, based on the ELISA method, enables the enumeration of lymphocytes secreting antibodies against one or more target antigens. Basically, the ELISPOT is a variant of the ELISA method, whereby antibody secreting cells (ASC) may be revealed by culturing lymphocytes in specially modified ELISA wells coated with the target antigen, and by replacing the standard ELISA reagents with enzyme-substrate complexes that yield a colored precipitate (spots), adjacent to the secreting cell. Spots can then be counted to give a measure of the number of antibody-producing cells. Protein synthesis inhibitors may be included in the culture medium, to confirm that the spots detected are due to de novo antibody synthesis, during the in vitro incubation period.

Whilst the ELISPOT technique has proved very useful in studying the dynamics of humoral immune responses, and has been used to detect spontaneous ASC that appear transiently in the peripheral circulation of immunized subjects, certain features of the method place constraints on its use in a clinical diagnostic setting. Firstly, since for each sample individual spots need to be counted which can be time consuming and laborious, the method is not particularly suited to the analysis of large numbers of samples, such as occurs in a clinical diagnostic laboratory. Secondly, only the number of cells secreting antibody in each sample is enumerated and generally speaking, this requires reasonably large sample volumes, e.g., several milliliters. ELISPOT plates are also expensive and the assay is not readily amenable to automation.

WO 96/26443 describes the use of a modified ELISA test which may be used to detect on-going antibody synthesis. In this assay lymphocytes are cultured after isolation and the levels of antibody produced during that culture period is determined. This technique thus necessarily requires incubation of the lymphocytes of the test sample at about 37° C. in order to allow measurement of the antibodies secreted during incubation. The average incubation period is 2-5 hours, which represents a significant limitation on the speed of performing the assay. Incubation also requires the provision of suitable equipment at the site of testing so that it may be carried out immediately prior to the assay procedure. This generally means that assay of the lymphocytes needs to be carried out shortly after a sample has been taken from a subject, because storage of samples, e.g., by freezing is not acceptable due to the resulting decrease in cell viability. Purified cells can only be maintained viable for relatively short periods of time by storage on ice at 0° C. or less favorably at 4° C.

It will be seen therefore, that despite advances in antibody detection techniques, there remains a need for a further improved assay which is simple, quick and cost effective to perform, which reliably enables precise quantification of spontaneously secreted antibody, which is able to distinguish the antibody synthesis, which may be performed on samples, e.g., blood samples, for diagnostic purposes. The present invention addresses this need.

In the above described technique, a period of culture was used in line with current thinking at the time on the assumption that this was necessary in order to obtain sufficient antibody titre for obtaining assay results for immunodiagnostic purposes.

It has been established in the literature that the biosynthesis of antibodies (immunoglobulins) takes place in B lymphocytes (see: Roitt I, Brostoff J, Male D. "Immunology", 4th Edition published by Mosby, London 1996, 6.12-6.13) whereafter they are secreted into the blood stream to fight infection. When secreted by antibody-secreting cells (ASC) the molecules are fully assembled (e.g. for an IgG molecule two heavy chains and two light chains joined by disulphide bonds) and glycosylated. The rate-limiting step in the biosynthesis of antibodies has been claimed to be the intracellular transport and glycosylation via the endoplasmic reticulum and Golgi complex (which takes 1 hour or more), whereas the biosynthesis of the various heavy and light chains of the immunoglobulins only needs minutes for completion. In total, the process of synthesis and secretion is estimated to take in the order of 2 hours (Melchers, 1971, Histochemical, J., 3, p 389-397). As a consequence of the rapid secretion of immunoglobulins from cells, it has never before been appreciated that functional antibodies, or even partially synthesized antibodies (e.g. preglycosylation) could be present within the lymphocyte cell in any significant amount. Furthermore it was not appreciated that disruption of lymphocytes in a sample could yield sufficient quantities of "newly synthesized antibodies" to allow detection for immunodiagnostic purposes.

SUMMARY OF THE INVENTION

It has surprisingly been found however that the cellular content of lymphocytes contains sufficient antibodies to allow detection and even quantification of acute antibody synthesis in a subject when the samples for analysis are taken during the acute phase of the immune response. This is generally at approximately the same time interval as would be expected for the appearance of antibody-secreting cells in peripheral blood. This thus provides useful information which may be used diagnostically.

Advantageously, this avoids the need to carry out lengthy incubation of the sample, e.g., a purified lymphocyte preparation, prior to assay since the assay does not require any incubation of the lymphocytes.

The assay of the invention also provides a reliable assay in which samples may be stored prior to preparing the assay e.g. by refrigeration (preferably at about or freezing, e.g. at less than 0° C. It will be appreciated by those skilled in the art that whole blood is preferably refrigerated (e.g., as described hereinafter) rather than frozen as freezing of whole blood will result in lysis of the cells. However, samples such as purified lymphocytes may be frozen or refrigerated prior to performing the assay of the invention without interfering in the test results. Thus samples may be stored for a prolonged period of time prior to assay even by methods which can affect viability of the cells, (e.g. in a similar manner to the storage of serum or plasma samples). As a consequence, the assay method of the invention offers significant advantages for sample collection, storage and processing, particularly allowing significant delay in performing the assay as may be necessary for laboratory testing of samples obtained in the field.

In one aspect, the present invention therefore provides a method of determining the presence or amount of newly synthesized antibody in a sample in response to an immunogen comprising:

obtaining a sample containing lymphocytes;

disrupting said lymphocytes whereby to release antibodies or parts thereof associated with said lymphocytes; and detecting the released antibodies or parts thereof whereby to determine the presence or amount of newly synthesized antibody in said sample.

As used herein, the term "newly synthesized antibody" refers to an antigenically active antibody (i.e. capable of recognizing and binding to the antigen corresponding to the immunogen) which has been produced or synthesized by and within a lymphocyte cell in response to the presence of an immunogen in vivo as part of an ongoing immune response. Thus, the antibody is synthesized by a lymphocyte during the course of an immune response triggered by the presentation of an immunogen in vivo, i.e. synthesized before and at the time the lymphocyte-containing sample is removed from the subject animal.

Reference herein to antibodies or parts thereof associated with said lymphocytes refers to newly synthesized antibodies or parts thereof which are antigenically active (i.e. capable of recognizing and binding to the immunogen) which have not yet been secreted from the cells. As mentioned previously, this will generally correspond to antibodies produced in the preceding 2 hours (which may occur exclusively in vivo or at least partially in vitro prior to cell disruption if the cells are, kept under appropriate conditions), although the time course of the secretion pathway may vary. Whilst antibodies may be produced rapidly within the cells (e.g. 1-2 minutes, although secretion is rather slower), free chains which make up antibodies or unglycosylated or partially glycosylated antibodies or antibody chains may be present in the lymphocytes, and hence released on their disruption. Where appropriate these "parts" may be detected and included in the measurement of the presence or amount of newly synthesized antibodies providing they are antigenically active as described above. Antibodies or parts thereof released from the lymphocytes comprise newly synthesized antibodies. Assessment of the levels of such newly synthesized antibodies provides relative information on the amount of active antibody production occurring in response to a particular immunogen, i.e. antibodies being produced as part of an ongoing, e.g. chronic or acute, immune response. The present invention thus also provides a method of determining the presence or amount of active antibody production by correlation to the levels of newly synthesized antibodies with reference to appropriate control samples.

The sample comprising lymphocytes may be taken from any animal, preferably mammalian e.g. human subject which has been presented with an immunogen prior to taking the sample. Usually, where the immune response is to be detected by the method of the invention, this will be caused by recent infection or vaccination, and it is desirable to take the sample within a few weeks or within a few days of exposure to the immunogen. The optimum time to take the sample from the subject will depend on the nature of the infection or the type of vaccine used, and is further determined by the efficiency of the subject s immune response mechanism, and this may vary between individuals. However, what is required is that the sample is taken at a time when the lymphocytes of the subject s immune system are in a phase of acute antibody synthesis in response to the immunogen of interest. Thus in general it has been found that the sample is conveniently taken within 3 weeks of presentation of the subject with the immunogen, more preferably within 8-12 days of infection or vaccination, but in some cases sufficient antibody production will occur within 1-5 days, or more specifically 2-3 days after infection or vaccination to obtain meaningful results from an assay in accordance with the invention.

The sample may be a blood sample or a sample derived from the lymphatic system of a subject. In general, any body fluid or tissue sample which contains lymphocytes from the immune system of the subject will be suitable. In particular, lymph or peripheral blood may conveniently be taken from a subject in a clinical or experimental environment, but any lymphatic or lymphoid tissue or any blood source comprising lymphocytes is equally suitable, including samples derived from lymph nodes or glands or from lymph nodules e.g. tonsils. Surgical intervention techniques have been developed which allow biopsy material to be taken from a subject and such procedures may be used where appropriate to obtain samples for use in the method of the invention. Depending on the source of the lymphocytes it may or may not be necessary to separate and purify the lymphocytes prior to assay in the method of the invention. However, where necessary or desired, the lymphocytes may be purified. Thus preferably, the sample used in the assay is a lymphocyte preparation prepared from one of the above mentioned sources by techniques known in the art.

By "disrupting" the lymphocytes is meant that the cell contents including any synthesized antibodies are released from within the confines of the cell membrane and internal membrane structures such that they may be detected by any convenient biochemical or chemical assay. It is known that immunoglobulins are synthesized and secreted during a pathway through the endoplasmic reticulum and Golgi complex. Thus, necessarily disruption requires release from these internal structures. Thus disruption of the lymphocytes may be achieved by known methods of cell disruption allowing release of the contents of membrane compartments, e.g. by cell lysis, for example using physical disruption means e.g. freeze-thaw cycles or by chemical means using cell-disrupting buffers or solutions.

As used herein the terms "detecting" and "determining the presence or amount of" encompass both quantitative and qualitative assessment of the level of antibody production, in the sense of obtaining an absolute value for the amount of antibody produced in the sample, and also an index, ratio, percentage or similar indication of the level of antibody production, as well as semi-quantitative or qualitative assessments. The term "determining the presence of" encompasses also situations where a negative result, indicating the absence of synthesized antibodies, is of value in assessing the immune response of a subject. For example a negative result may be indicative of the absence of an immune response to the immunogen of interest or may be indicative of chronic infection if antibodies to the immunogen of interest are present in serum.

Detection of newly synthesized antibodies allows assessment of the levels of such antibodies specific to one or more immunogens, rather than an assessment of all antibodies present within the cells.

Detection of the synthesized antibodies may be by any method which allows for identification of those antibodies which bind to the immunogen of interest causing the immune response. Thus any detection technique which results in the production of a signal which reflects the presence of the target antibody may be used. For example enzyme-linked assays may be used in which a soluble or insoluble product may be produced from a substrate, whose amount may be assessed.

Conveniently the synthesized antibodies may be detected for example by means of a solid phase binding assay, e.g. an ELISA, wherein they bind to the antigen used in the assay, although the antigen used may be different to the immunogen stimulating the immune response in the first place. Thus, whilst both the antigen used in the assay and the immunogen which has stimulated or is stimulating the production of antibodies in vivo would bind to the antibodies to be detected by virtue of identical or very similar epitopes, in other respects the antigen and immunogen may not be identical. Thus, whilst the antigen used in the method of the invention may be material containing all or some parts of the relevant immunogen, e.g. derived from infected individuals, or purified parts from the same or similar material, the antigen may similarly be prepared synthetically, e.g. by chemical synthesis or recombinant expression, with added or deleted portions relative to the native antigen. Thus fusion proteins, or molecules expressing only the appropriate epitope(s) may be used.

The present invention provides several advantages over known antibody assay techniques. Firstly, in contrast to techniques which detect serum antibody levels (e.g. serum ELISAs), the present assay detects antibodies which are indicative of a current infection/immune stimulation, or in the case of neonates allows separation of maternal and neonate antibodies. This is possible since lymphocytes from the sample are used directly in the assay method of the invention without any other form of prior treatment or stimulation, e.g. in vitro stimulation by antigen. The antibodies being synthesized by the lymphocytes at the time of sampling may thus be detected. (In this way, even using small sample volumes, spontaneous ongoing antibody synthesis in response to the immunogen of interest may be distinguished from bystander activation of lymphocytes.) Also the assay is carried out on lymphocytes which have been disrupted during the stage where they spontaneously produce and secrete, or are beginning to secrete antibodies, without stimulating the cells to reveal any memory. This is in contrast to other published methods which take advantage of in vitro antigenic stimulation which may increase the sensitivity of the test but which reveals cell memory and therefore is not an accurate or suitable technique for detecting acutely-made or newly synthesized antibodies in response to a current infection or recent vaccination.

The present invention on the other hand takes advantage of spontaneous antibody secretion to permit the detection of antibodies in blood indicative of an ongoing infection by the test antigen; plasma lymphocytes will secrete antibody against the test antigen in the first few weeks following infection, or vaccination etc. Detection of such antibodies by the method of the present invention enables infection to be diagnosed or determined, or the antibody response to vaccination to be monitored etc.

Thus in a further aspect the present invention provides a method of diagnosing or monitoring infection of a human or non-human animal or a part of said animal by an immunogen by performing the method of the invention and determining the presence or extent of infection by said immunogen by reference to appropriate controls and/or reference samples.

The method of the invention is particularly useful in infants and neonates, where it is important to distinguish newly synthesized antibody from passively transferred maternal antibodies. The same lymphocyte-containing sample may be analyzed for antibodies against several distinct infectious agents either in separate assays or in the same assay using multiple relevant antigens, thus allowing for use of relevant contacting antigens consistent with the clinical syndrome with which the patient presents.

In diagnosing infections, it is also important to be able to distinguish ongoing antibody synthesis from antibodies already existing from an earlier infection. Recalling immunological memory by antigenic stimulation in vitro is not consistent with an assay aimed at identifying an ongoing acute infection, and hence prior methods based on antigenic stimulation do not share this advantage. Also, including the step of antigenic stimulation would compromise the beneficial time factor of the assay of the invention, which is very quick to perform compared with prior art methods.

Secondly, in contrast to techniques which detect antibody secreting cells or actively secreted antibodies, in the present invention, although acute antibody synthesis forms the basic parameter for detection, there is no need to maintain the sample in conditions which promote synthesis and/or secretion of antibodies. This greatly simplifies the test and is particularly beneficial in comparison to the previously known assay disclosed in WO96/26443 which requires incubation of the lymphocytes after sampling, and also maintenance of conditions during the assay which allow the lymphocytes to continue secreting antibodies.

A particularly surprising benefit of the present invention has been the avoidance of any incubating step or special assay conditions, and this means that samples may conveniently be treated after sampling in order to effect disruption or lysis of the cells, and the lysate can then be stored e.g. by freezing or refrigerating for a period of time before the assay step is carried out. Alternatively, as mentioned previously, the sample e.g. whole blood or a purified preparation can be stored e.g. by freezing or refrigeration (as appropriate, depending on the sample) for a period of time e.g. for up to several hours or days, e.g. for more than 4 hours, before the cells are disrupted. For example, a purified lymphocyte preparation could be stored by freezing for a period of time e.g. for several hours or days, or by refrigeration, e.g. for a few hours, if necessary or desired, before the sample is treated to disrupt the cells. Thus for example, purified lymphocytes could be stored at 4° C. for several hours e.g. for up to 4 to 6 hours before treating them to disrupt or lyse the cells.

However, it has surprisingly been found that some samples e.g. whole blood preparations can be stored under refrigeration for longer periods of time without adversely affecting the cells and interfering in the test results. For example it has been found that whole blood samples can be stored under refrigeration (e.g. at 4° C.) for at least 6 days, and if desired the samples can be intermittently kept at room temperature (18-25° C.) for at least 6 hours, before procedures for purifying lymphocytes are initiated, without adversely affecting the performance of the test. This is particularly useful when blood samples are on hold in the laboratory and are stored under refrigeration while results from routine or supplementary plasma/serum testing procedures are pending. This is surprising and unexpected, since it implies that the physical integrity of the lymphocytes is maintained during storage, thus allowing subsequent lymphocyte purification from the stored blood (if desired) and disruption of the lymphocytes to take place, without a significant reduction in the antibodies being detected.

Thus, in a preferred embodiment prior to disruption of the lymphocytes, e.g. where the sample is blood the sample may be stored for several days e.g. up to about 6 days or more, especially when stored under refrigeration at about 4° C. even allowing for removal of the sample from its refrigerated environment for intermittent periods of e.g. 4 to 6 hours for example at room temperature on two or more occasions during the storage period, without adversely affecting the results of the assay. This is particularly useful when blood samples are stored under refrigeration but where it is unavoidable that the sample be left on the bench at room temperature for a short time. Surprisingly, it has been found that cell viability is not sufficiently affected to interfere with or prevent acceptable results being obtained according to the assay method of the invention. In a further preferred embodiment, when purified lymphocyte preparations are used, these samples may be stored at less than 4° C. (e.g. for several days or longer) or stored at above 4° C. (for up to 6 hours). The possibility of storing various samples for use in the assay makes the method of the invention particularly suitable for larger diagnostic laboratories when expensive automated laboratory equipment e.g. ELISA hardware can be most efficiently run using a substantial number of samples at one time. It also means that samples may be taken in many different locations and mailed or delivered to a central diagnostic laboratory for analysis in a similar manner to procedures set up for analysis of chemical serum samples in other types of tests. Thus viewed from an alternative aspect, the invention provides a method of determining the presence or amount of newly synthesized antibody in a sample in response to an immunogen comprising detecting the released antibodies or parts thereof in a sample containing lymphocytes which have been disrupted whereby to release the synthesized antibodies or parts thereof associated with said lymphocytes whereby to determine the presence or amount of newly synthesized antibody in said sample.

A major advantage of the present invention is that only small sample volumes are required. As few as 100,000 lymphocytes or even less than 50,000 lymphocytes may produce a detectable signal in the method of the invention. Since e.g. 1 ml blood comprises 1×106 lymphocytes, if the method of the invention is used to assay lymphocytes derived from blood as little as 50 or 100 µl blood may be used to provide sufficient lymphocytes for performance of the invention. Even taking into account appropriate control tests (e.g. blanks and test positives) as little as 150 to 300 µl may be used to provide diagnostic results. Clearly at least some control samples may be waived once the test is standardized. Thus conveniently the test of the invention requires e.g. 50-500 µl, preferably 100-300 µl and commonly 100-200 µl, of lymphocyte-containing sample in a comparable volume to the whole sample source. Thus the method of the invention may use e.g. $5 \times 10^4$ to $5 \times 10^5$, preferably 1 to $2 \times 10^5$ lymphocytes. This is in contrast to classical diagnostic tests which generally rely on several milliliter volumes of serum or other fluid. This is especially useful in the case of blood sampling where only small samples are available, e.g. from neonates as the method of the invention requires only microliter volumes which may be taken for example by capillary tube from a suitable site such as from the ear-lobe, finger tip or heel.

Thus, the method of the invention permits the use of small blood sample volumes (e.g. microliter volumes, less than 1 ml, preferably less than 500 µl, e.g. less than 100 µl) directly to detect the spontaneous or de novo antibody production by unstimulated lymphocytes, without a prior step of pre-culturing the lymphocytes prior to assay.

Antigens or immunogens to which antibodies for detection according to the method of the invention are directed include both bacterial and viral antigens. Clinically important antigens include, but are not restricted to those from for example Herpes Simplex virus, Cytomegalovirus, human immunodeficiency virus (HIV) and any of the Hepatitis viruses as well as Toxoplasma and Epstein-Barr virus (EBV). In general, however, any immunogen arising as a result of an infection or vaccination eliciting a clear antibody response (e.g. during the acute phase) may be detected by the method of the invention. In cases where chronic infection results in detectable levels of target antibodies within lymphocytes, assay of these antibodies may also be performed according to the method of the invention. Thus for example, antibodies to any immunogen which may be detected using a conventional ELISA method may be detected by the method of the present invention. Detection of antibodies to such antigens could be used to rapidly establish whether patients are infected e.g. for blood screening purposes or for establishing and/or monitoring infection.

The present invention thus further provides a method of diagnosing or monitoring infection of a human or non-human animal or a part of said animal by a bacterium or virus, wherein said method comprises obtaining a lymphocyte-containing sample from said animal, determining the presence or amount of newly synthesized antibodies or parts thereof associated with said lymphocytes directed to said bacterium or virus according to the method described herein and determining the presence or extent of infection by said bacterium or virus by reference to appropriate control and/or reference samples.

The method is particularly useful owing to its simplicity and may be used when elaborate equipment is not available e.g. in field situations. With no requirement to incubate the sample as part of the assay method, the method is readily susceptible to automated procedures but it is also relatively quick and simple to carry out cell lysis and antibody detection in situations where complex equipment is not available.

Figure 1:
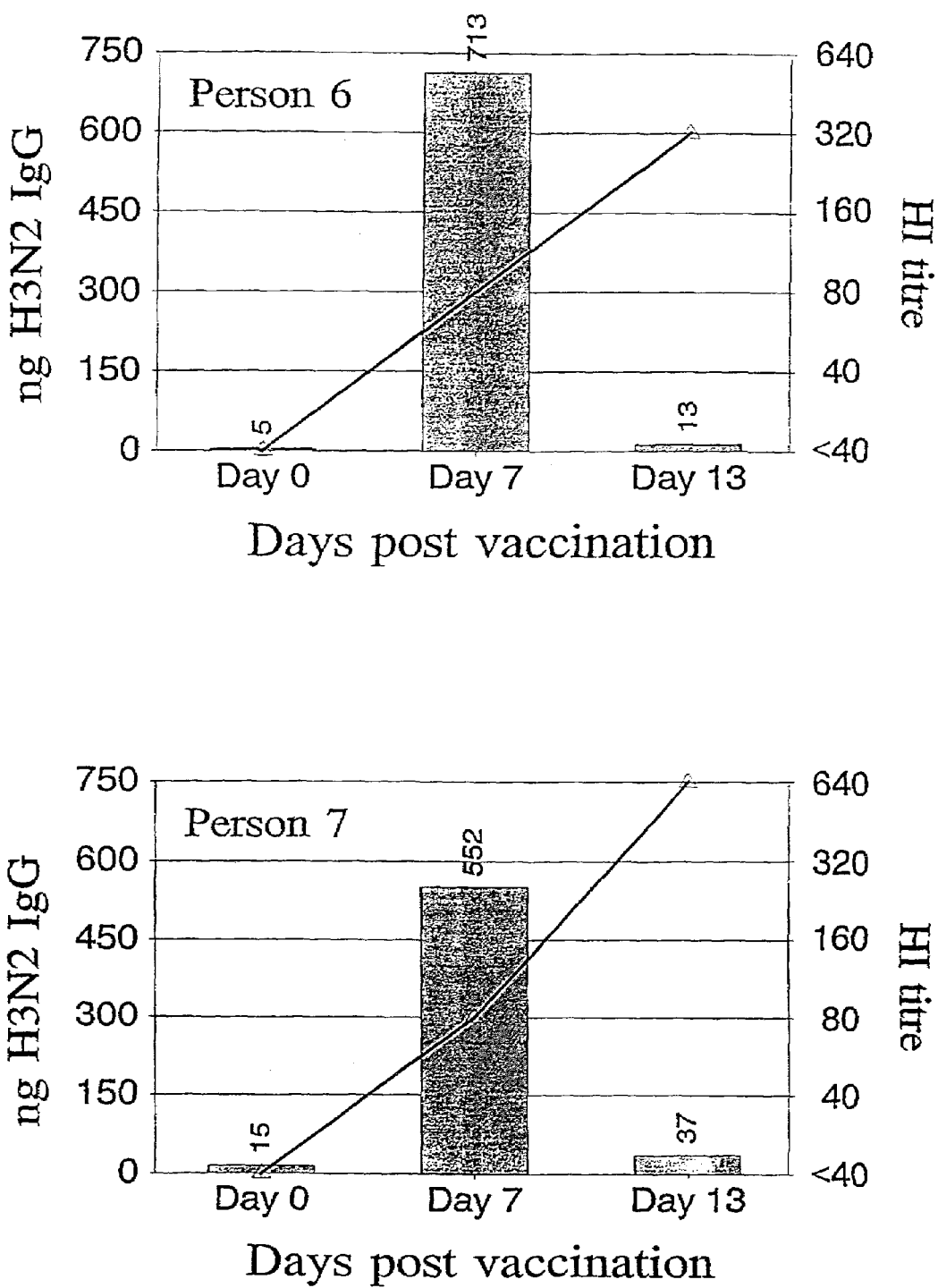
FIG. 1 shows the results of a clinical influenza vaccine trial in which samples from 9 subjects (persons 2 to 10) were tested using the lymphocyte disruption method. The left-hand scale on each bar graph shows H3N2 IgG plotted in ng against days post vaccination on the horizontal scale. Superimposed on each bar graph is a dotted line showing the HI titre on the right hand scale for A/Nanchong virus. See Examples 1 and 2 for further details.
Figure 1:
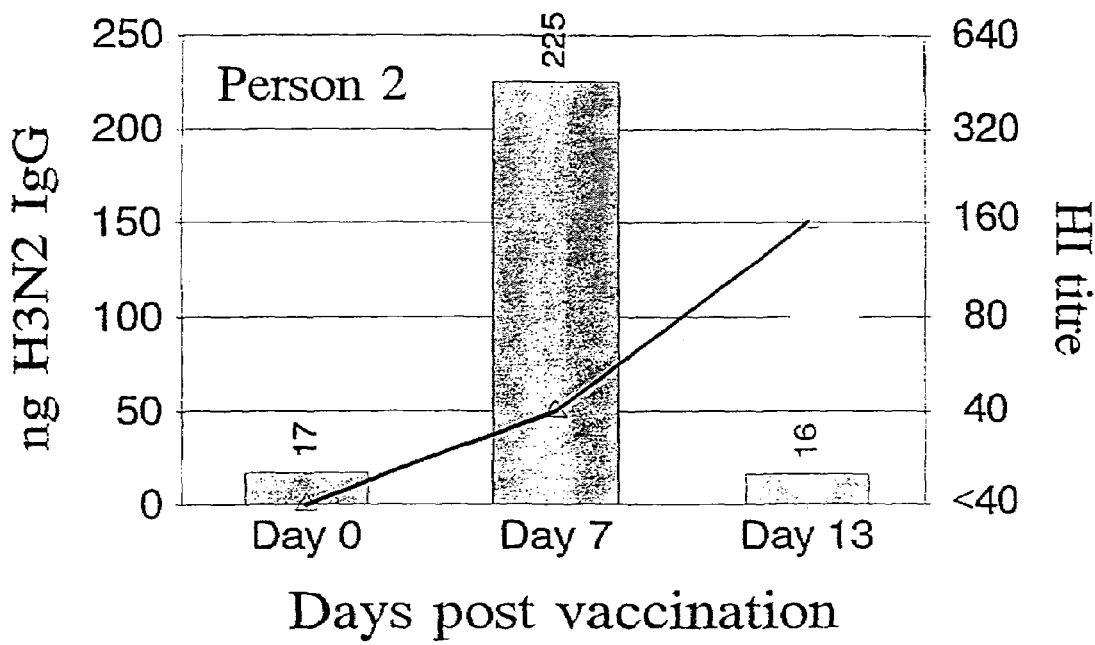
Figure 1:
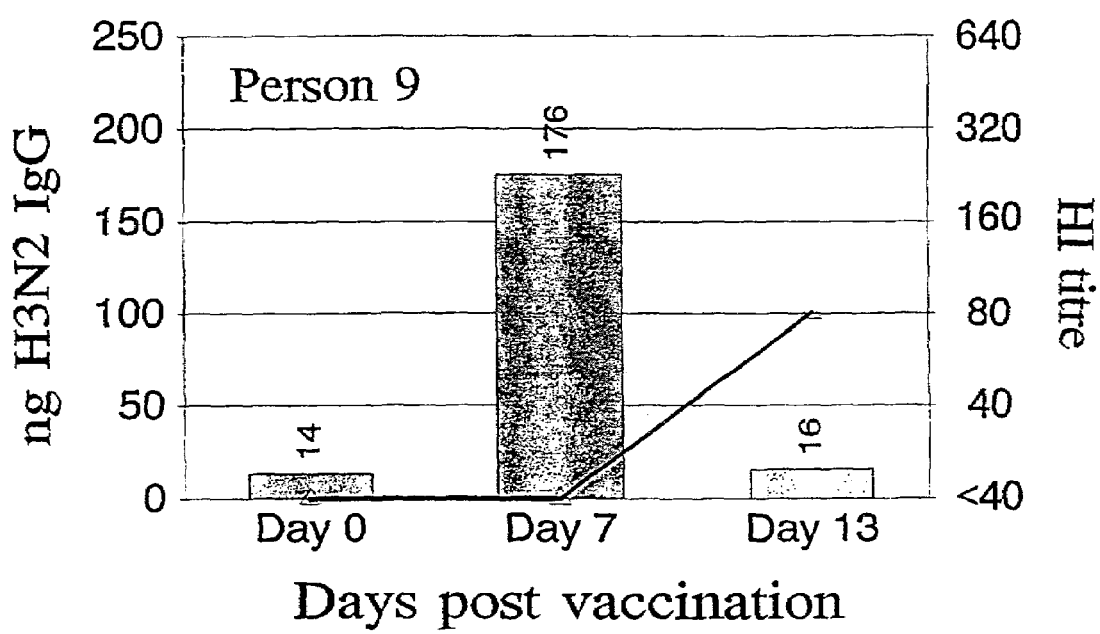
Figure 1:
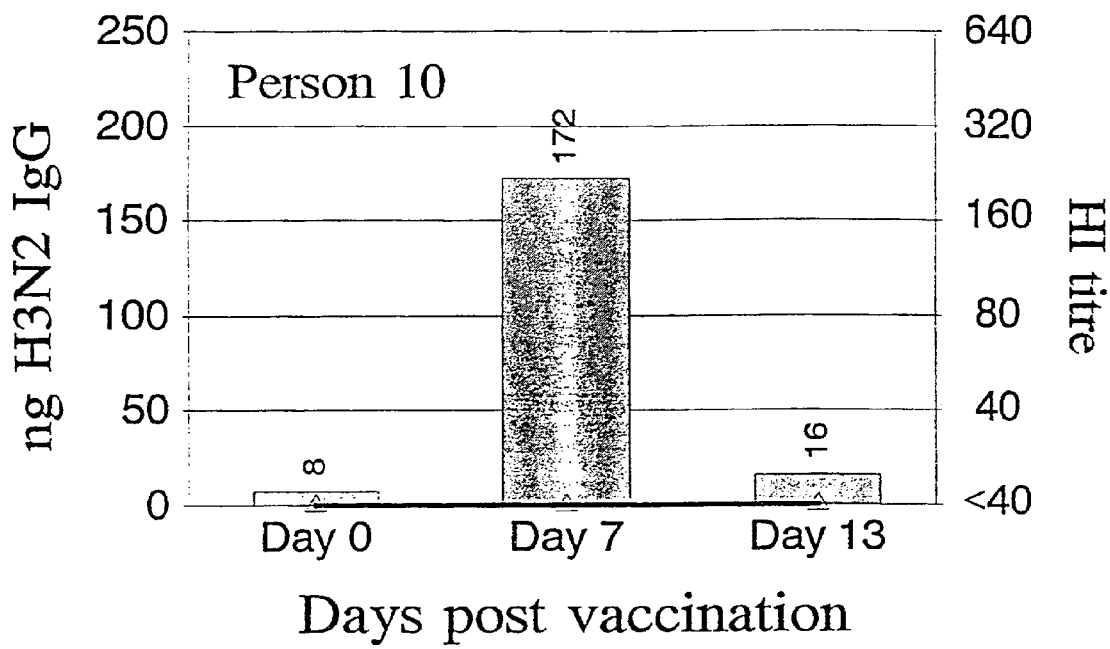
Figure 1:
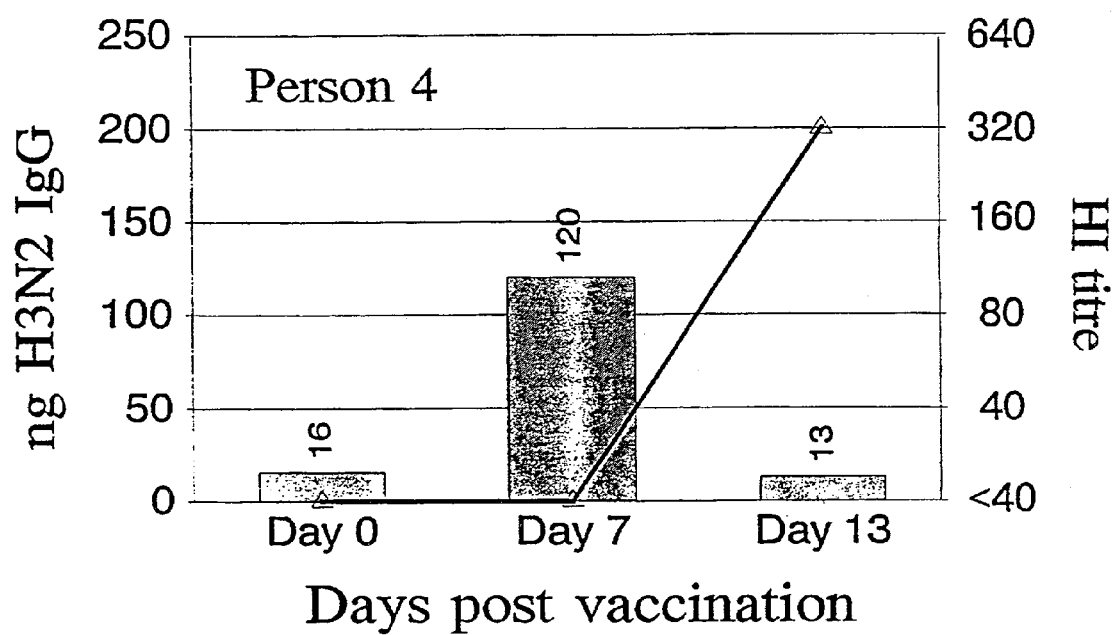
Figure 1:
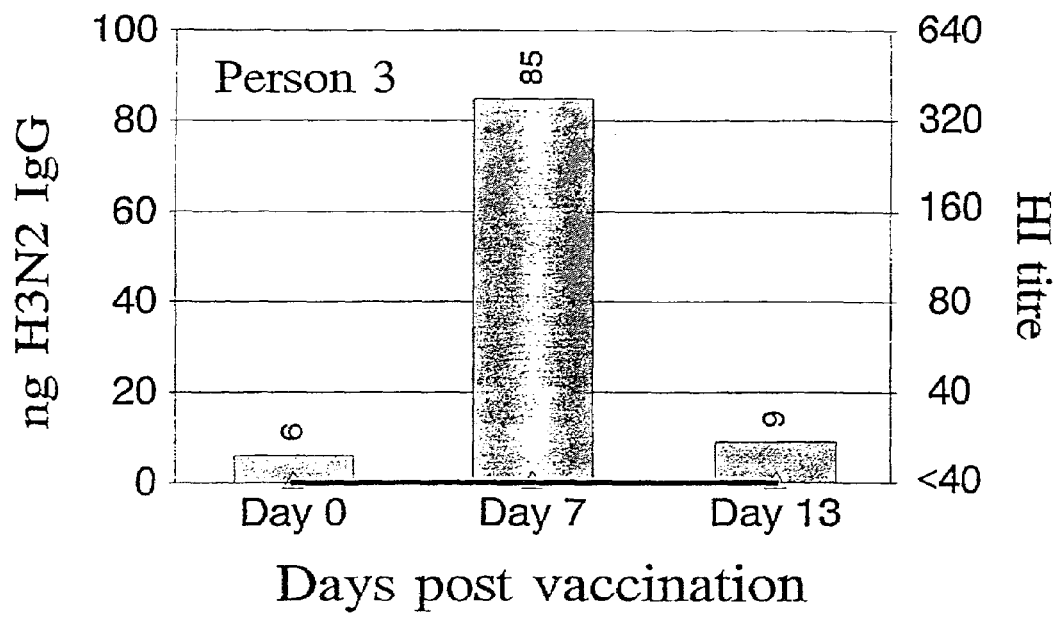
Figure 1:
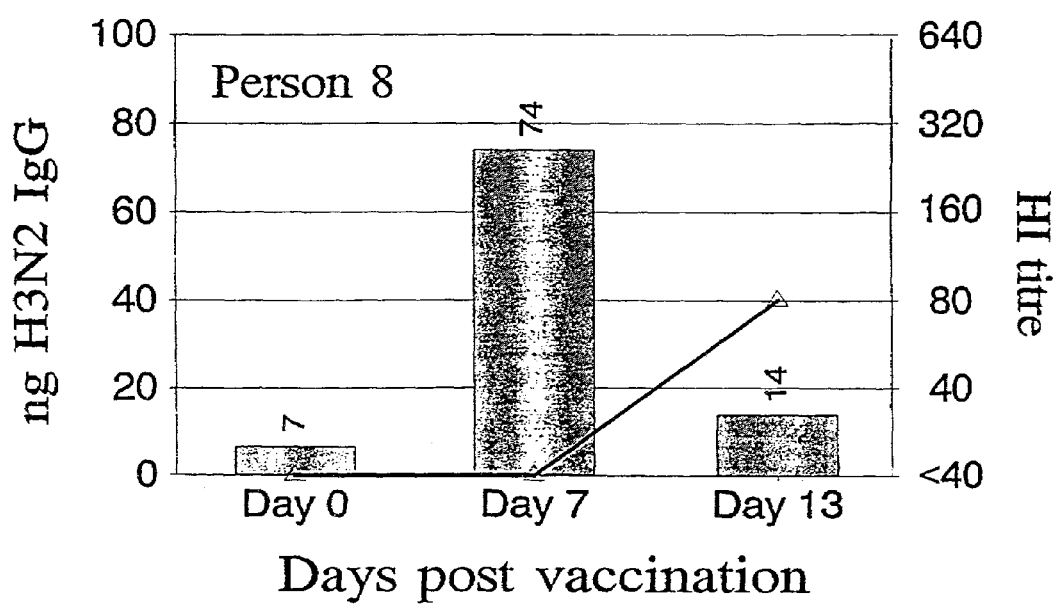
Figure 1:
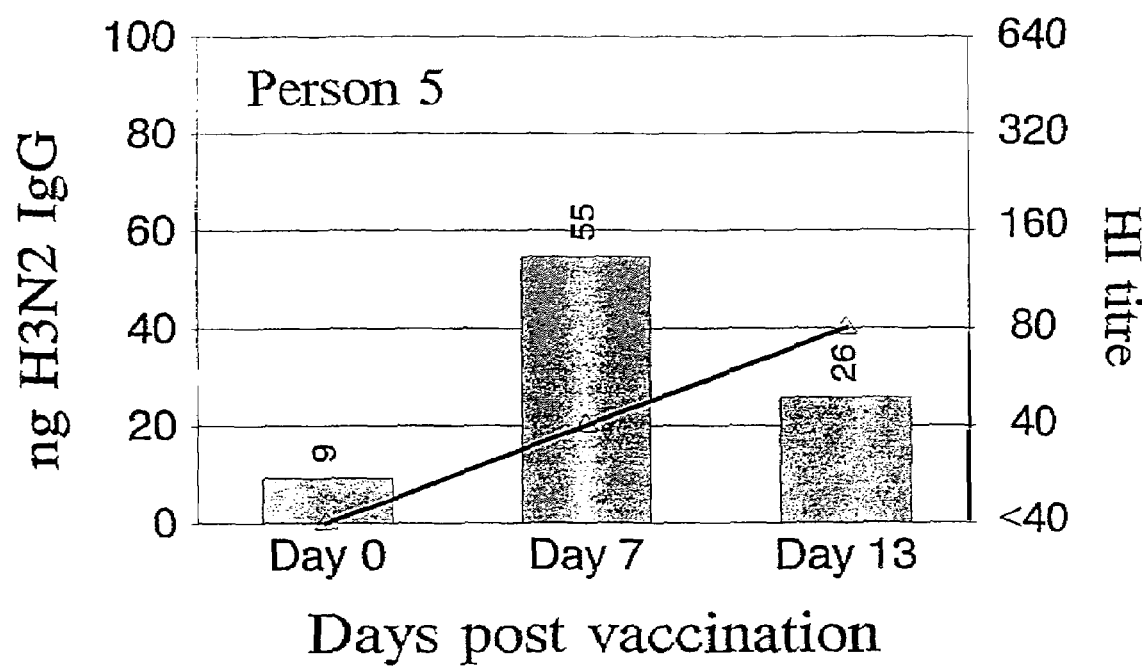

The invention will now be described in more detail with reference to the following non-limiting Examples.

DETAILED DESCRIPTION OF THE INVENTION

The method of the invention will now be described in more detail. Preferably the first step in the method comprises isolation of lymphocytes from the sample. As mentioned previously however, a purified lymphocyte preparation is not necessarily required and instead, a preparation in which the majority of plasma antibodies have been removed may be used. Preferably such a preparation may contain less than 15% of the antibodies contributed by the plasma antibodies present in the sample, e.g. less than 5%, preferably less than 1%. Conveniently this may be achieved by employing an essentially plasma-free preparation (e.g. less than 5% (v/v), e.g. a serum-free preparation. A lymphocyte preparation can be prepared using standard techniques, well known in the art e.g using filter methods or techniques using absorbent material or lymphocyte preparation kits. Thus, for example, various whole blood preparations may conveniently be used to obtain the lymphocytes e.g. from heparinized blood, EDTA-blood etc., such as are routinely prepared in clinical laboratories. It will be appreciated that all enriched or purified preparations must contain the lymphocytes present in the sample from which the preparation is derived to allow detection of spontaneous or de novo antibody production.

Preferably the lymphocytes are separated, for example using standard lymphocyte separation media eg. Lymphoprep (Nycomed Pharma AS, Oslo, Norway), or using immunomagnetic separation (IMS) or a similar solid phase based separation system or other common techniques. In the case of EMS or similar separation techniques, a solid phase e.g. magnetic beads coated with antibody specific for certain sets of leucocytes may be used to separate the useful lymphocytes selectively. Where separated lymphocytes are used, the cells may be washed prior to use, using standard washing methods. Preferably, the lymphocytes are washed in order to remove any plasma antibodies which may be present after cell separation. In general, in order to perform the invention, contamination of lymphocyte cells by plasma antibodies is kept to a minimum, preferably below 20 ng plasma IgG per 100 µl sample, representing approximately a 1:50,000 final dilution factor of plasma, e.g. below about 0.5 ng serum IgG per 100 µl sample. It has been observed however, that in order to achieve this, excessive or extensive washing of the cells is not required. For example, it has been found that by simply centrifuging whole blood diluted with buffers three times under approximately the same conditions of spin, a preparation of lymphocytes sufficiently free from contaminating serum/plasma antibodies can be obtained. See Example 3 for further details.

Generally speaking, the method of the invention avoids the need to incubate lymphocytes from the sample prior to performing the assay. It will be appreciated however that if the cells are maintained for short periods of time under conditions allowing continued production or secretion of antibodies prior to disruption of the lymphocytes that the method of the invention will still allow assessment of newly synthesized antibodies associated with the lymphocytes.

The sample to be analyzed, having been treated as mentioned above if required to obtain the separated lymphocytes, are then disrupted to release newly synthesized antibodies. This may be performed by any convenient technique known in the prior art which effectively disrupts external and internal membrane structures without affecting the ability of the released antibodies to bind to their complementary epitopes, e.g. by the use of detergents, chaotropic agents, disruption buffers e.g. containing EDTA or alternative disruption methods such as sonication or physical disruption through generation of shear stresses. Preferably, however a disruption buffer is used as this is generally the simplest and most convenient technique e.g. as described in the Examples herein i.e. buffer containing detergent such as 0.5% deoxycholate. Appropriate disruption buffers may be used to stabilize the released antibodies, e.g. to control pH or degradation. Thus for example buffers containing protease inhibitors may be employed if necessary. Alternative methods of disruption include for example the use of freeze/thaw cycles or even the use of liquid nitrogen. This results in a lysate in which the released antibodies are in solution which is used for subsequent steps. It will be appreciated that in order to obtain sufficient amounts of newly synthesized antibodies in the sample to be detected, it is desirable that as many of the lymphocyte cells as possible are disrupted to release the antibodies. Preferably, then, the disruption means is suited to this end and at least 40% or 50%, more preferably at least 60%, 70% or 80% and more preferably at least 90% of 95% of the lymphocytes in the sample are disrupted. After disruption of the lymphocytes the antibody content of the sample is assessed by an appropriate technique allowing detection of the target antibodies. Conveniently to achieve this, the sample may be contacted with a solid phase carrying an appropriate binding partner to immobilize the antibody or antibodies to be detected. Conveniently the binding partner is the antigen (immunogen) or antigens (i.e. one or more), recognized by the antibody or antibodies or parts thereof to be detected. In one embodiment, the present invention thus provides a method of determining the presence or amount of newly synthesized antibody in a sample, said method comprising: contacting, aliquots of said sample, or optionally, of lymphocytes directly isolated from said sample wherein said lymphocytes have been disrupted to release antibodies or parts thereof associated with said lymphocytes, with one or more antigens, preferably carried on a solid phase, recognized by the antibody or antibodies to be detected; detecting binding of antibody to said antigen(s); and comparing said antibody binding to control and/or reference samples, whereby to obtain a determination of the presence or amount of newly synthesized antibody in response to said antigen(s). In the above method, control or reference samples may be appropriate negative or positive controls, e.g. blanks, normal samples or spiked samples.

Alternative binding partners may also be used, for example protein A, protein C or antibodies which recognize and bind to the antibody to be detected. In the latter case, highly specific binding is not required as specificity is introduced in this embodiment of the assay method by the subsequent binding of antigens which bind specifically to the antibodies to be detected. Thus in all embodiments a, specific antigen-antibody complex is created. The presence of such complexes, preferably immobilized to a solid support, is ascertained in the detection step of the method of the invention. Thus in a preferred feature the detection step of the method of the invention comprises detection of the released antibodies or parts thereof by the formation of an antibody:antigen complex wherein said antigen (which preferably is not an antibody) comprises or contains the immunogen or a part thereof containing at least the epitope of the immunogen.

The solid phase, when employed, may be any of the well-known supports or matrices which are currently widely used or proposed for immobilization, separation etc. These may take the form of particles, sheets, gels, filters, membranes, or microtitre strips, tubes or plates etc. and conveniently may be made of a polymeric material. However, for ease of operation and simplicity standard microtitre plates and wells may conveniently be used, preferably standard ELISA plates.

The solid phase may also be modified to permit detection of antibodies specific for a range of different antigens. Thus for example, discs or strips etc. of a suitable solid phase material eg. nitrocellulose or such like may be coated with different antigens and added simultaneously to a microtitre well or other suitable vessel, not containing any contacting antigen. Antibody binding detection methods may then be used to distinguish between the different antigens. Conveniently when sandwich-type assays are employed, the solid phase carries one or more antigens (solid phase antigens) recognized by the antibody or antibodies or parts thereof to be detected (target antibodies) Alternatively, the solid phase may carry one or more antibodies (solid phase antibodies) which recognize the antibody or antibodies or parts thereof to be detected (target antibodies). To allow detection according to the method of the invention, as appropriate, depending on whether the said solid support carries antibodies or antigens as described above, one or more antigens, recognized by the target antibodies immobilized on said solid phase, are contacted with said solid phase or alternatively one or more antibodies, which recognize target antibodies immobilized on said solid phase, are contacted with said solid phase. These antigens or antibodies which then become bound to the solid support may be appropriately labeled to allow detection as described hereinafter.

Sets of discs each coated with relevant antigens consistent with a certain clinical condition or syndrome may be used in order to identify which of the suspected agents is causing the disease. The discs would then be individually processed in separate wells. This is a particularly material-saving procedure, since tests can be performed for simultaneous testing of a multiplicity of different antigens (either from the same infectious agent or from different agents relevant for the clinical syndrome or condition in each case) using the same small blood volume. An alternative approach is to use multiple samples of disrupted lymphocytes i.e. in separate wells, each coated with different binding partners, e.g. antigens or antibodies, and develop the test accordingly.

Techniques for binding of the binding partner, e.g. antigen to the solid phase are also extremely well known and widely described in the literature. Many standard antigen coating procedures are described for example in ELISA and other solid phase Immunoassays, Theoretical and Practical Aspects; 1988, ed. D. M. Kemeny & S. J. Challacombe, John Wiley & Sons. If desired, the plates may be washed and blocked, again using standard techniques. Thus, for example, standard microtitre plates eg. ELISA plates may simply be coated with binding partner by incubating the plates overnight at 4° C. in a suitable buffer e.g. phosphate buffered saline (PBS) containing the binding partner e.g. at concentrations of 0.01 to 150 μg/ml protein, followed by blocking using appropriate blocking media (generally a neutral buffer, such as PBS, containing a blocking protein e.g. calf serum or proteins from dried milk) and incubating eg. at 37° C. for 1 to 5 hours. After removing the blocking solution the plates are ready for use.

Conveniently, however, the materials required to perform the method of the invention may be provided in kit form, where the solid support is supplied ready coated with binding partner and appropriately blocked.

It may be desirable to dilute the disrupted lymphocyte sample suspension prior to the contacting step, and conveniently a range of cell/sample dilutions may be used. Dilution will generally be performed using the buffer in which lymphocytes are disrupted as diluent.

The binding of the antibody to its antigen is then detected. The detection step, in terms of reading the signal, conveniently takes place in solution. However, an insoluble product or signal may be generated which is not read in solution. Any of the known means of detecting antibody binding may be used, as long as a readable signal is generated; for example depending on fluorescence, chemiluminescence, colorimetry or an enzyme reaction to produce the detectable signal. Where a solid phase is not used, the released antibodies may be detected by any other sensitive serological method such as light scattering (e.g. nephelometry) and resonance procedures. Conveniently, an immunoassay may be used as the means of detection, and preferably an enzyme-linked immunosorbent assay (ELISA). However, test procedures other than ELISA are contemplated within the scope of the invention for detecting antibodies. Techniques which use coated discs or glass plates, for example, flooded with a suspension of disrupted lymphocytes may be suitable. Any standard technique for detecting antibodies known in the art, such as techniques which result in an insoluble or soluble product, may be adopted for use in the method of the invention either for quantitative analysis or for a qualitative (e.g. yes/no) type of test.

Immunoassay, and particularly ELISA, techniques are well known in the art and described in the literature (see for example ELISA and other solid phase Immunoassays, Theoretical and Practical Aspects; 1988, ed. D. M. Kemeny & S. J. Challacombe, John Wiley & Sons).

Following the contacting of the disrupted lymphocyte sample, an enzyme-antibody conjugate may be added, for example in the ELISA detection method, which binds to the antibody bound to the antigen on the solid phase. Similarly, if the antibody to be detected is bound to the solid phase non-specifically via a binding partner, for example by an antibody against antibodies of a different species, an enzyme-antigen conjugate may be added which will bind specifically to the immobilized antibody to be detected. An enzyme substrate is then added in order to develop the detectable signal. In the present invention, a soluble substrate is conveniently used, yielding a signal detectable in solution. This is advantageous since it facilitates and simplifies the handling and processing of a large number of samples, and permits estimation of antibody production, although as mentioned above, absolute quantitation is not necessary, and if desired a qualitative or semi-quantitative result may be obtained. For convenience the substrate may be selected to yield a spectrophotometrically detectable signal, which may simply be read by reading absorbance, eg. using a standard ELISA plate reader. Indeed, standard ELISA reagents may be used, which has the advantage of rendering the assay of the invention compatible with existing methods, and techniques routinely employed in clinical laboratories. However, other detection/signal generating systems may be used, yielding signals detectable by fluorescence, chemiluminescence etc.

Immuno-enzymatic amplification methods may also be used to improve the signal and increase sensitivity, for example using avidin-biotin methods such as the Extravidin system available from Sigma. Biotinylated secondary antibodies are used as ELISA reagents, in combination with a peroxidase avidin complex. Since one molecule of avidin is capable of binding several molecules of biotin, the use of avidin-biotin peroxidase complexes increases the surface concentration of peroxidase molecules, giving the method even greater sensitivity.

The materials and means required for the lymphocyte disruption step and the antibody-binding detection step may also be conveniently supplied in kit form together with the binding partner-coated solid phase.

The information obtained from the assay of the invention may be supplemented by using other assay methods. Additional and useful data on pre-existing serum/plasma antibodies may be obtained in a classical ELISA test. Additionally, after separation of lymphocytes from the blood sample, the remaining plasma fluid may be used for detecting pre-existing antibodies using the same binding partner-coated solid phase used in the assay of the invention.

In order to ensure that the assay method of the invention is working confidently, appropriate controls may be included and used for determining the presence or amount of newly synthesized antibody. For example, to ascertain that the recorded signal from test wells is not due to sporadically and nonspecifically (bystander) activated lymphocytes, a negative control antigen is used. This antigen would be from an infectious agent most unlikely to be responsible for the acute disease of the patient, e.g. tetanus toxoid. The numbers of such bystander activated lymphocytes will in any event in all circumstances be much lower than required for a positive test result using the method of the invention. The design of the invention takes this point into account.

As mentioned above, due to its ease and speed of operation and simplicity, the assay of the invention, lends itself to diagnostic or other clinical or veterinary uses, e.g. fish-farming. In addition to small sample volumes, a further advantage is that only one sample is required, rather than serum pairs taken at a 2 to 3 week interval, such as is required in most conventional serological tests. Elaborate instrumentation is not required, and the assay is readily automated. In addition, it should be possible to test for different immunoglobulin isotypes if required.

The afore-mentioned assay method of the invention provides one method for assessing the presence or extent of ongoing infection by virtue of the analysis of the spontaneous expression of specific antibodies to a defined antigen. Such a method is clearly applicable to the assessment of disease conditions which are known and to which antigens related to the relevant immunogen are available and thus provides a specific marker of infection. In some clinical situations however the specific disease or infection may not be identified and/or the appropriate antigen may not be available for use in the assay. In such cases, the assay may be modified to assess for the presence or extent of nonspecific indicators of infection. Thus for example, lymphocyte-containing samples e.g. whole blood or purified or enriched lymphocyte preparations therefrom, may be examined with regard to their production of infection markers e.g. cytokines or interferons, for example IL-2, IL-4 or interferon-y.

Thus viewed from a yet further aspect the invention provides a method of determining the presence or amount of infection indicators in a sample in response to an immunogen comprising:

obtaining a sample containing lymphocytes;
disrupting said lymphocytes whereby to release the infection indicators to be detected; and
detecting the released infection indicators whereby to determine the presence or amount of infection indicators in said sample.

For performing this method, the solid phase may be provided with appropriate capture molecules, for example antibodies to the infection indicators for detection. For detection of the presence of said infection indicators immobilized on the solid phase, methods as described hereinbefore may be used, for example by the use of labelled antibodies or ligands. In this method, specific markers may be identified by appropriate choice of the immobilizing moiety or detection molecule. Thus, for example, all protein in the sample may be immobilized on the solid support and detection may be performed using a labeled specific antibody or ligand. Alternatively, a specific binding partner may be used to immobilize pertinent infection indicators which may then be labeled appropriately, either positively or negatively, for example in the former case by binding to a domain present on the infection indicator but not exclusive to that molecule, or in the second case by labeling unbound binding partner on the solid phase. Kits for performing this method also form part of this invention.

EXAMPLES

Example 1

Specificity

Subject: Initials LOH, male, 25 years. Blood sample taken 9 days post first day of classical clinical influenza-like illness. A mixed epidemic of influenza A and B had been recorded in the local community.

Separation of lymphocytes: Peripheral heparinized venous blood sample was collected. Lymphocytes were separated by Lymphoprep (Nycomed Pharma AS; Oslo) according to the manufacturer s instructions, except that the heparinized blood sample was mixed with a double (instead of an equal) volume of phosphate-buffered saline (PBS, pH 7.2) before first centrifugational step. Two extra washing cycles of cell pellet was performed. The numbers of lymphocytes were counted in a haemocytometer using the Blue Dextrane exclusion method.

Disruption of lymphocytes: Graded amounts of lymphocytes were disrupted by the DISRUPTION BUFFER 10 mM Tris HCl H 7.4), containing 0.5% deoxycholate, 2 µg/ml pepstatin A (Sigma P-4265, lot 18H0551), 2 µg/ml leupeptin (Sigma L-0649, lot 77H86221), 0.5% aprotinin (Sigma A-6279, lot 87H7010), 1 mM PMSF (Sigma P-7626, lot 48H1265) (based on reference: Spector D L, Goldman R D, Leinwand L A. Cells. A Laboratory Manual. Cold Spring Harbor Laboratory Press, New York, 1998, Vol 1: 74.6) and subjected to ELISA testing (see Table 1).

Coating and blocking of ELISA plates: Greiner microplate F-form, medium binding capacity, Cat #655001 (lot 98 26 01 48), D-72636 Frickenhausen, Germany. Virus antigens (a gift from Solvay-Duphar, Holland) for testing for influenza antibodies: A/Nanchang/933/95 (H3N2) surface antigens, 10 µg/ml in PBS, 100 4/well. B/Harbin/07/94 surface antigens, 10 µg/ml in PBS, 100 µl/well. For testing for general IgO antibodies: Goat anti-human IgO (y-chain specific) Sigma 1-7883 (lot 76H8895) used at 1:500 dilution in PBS, 100 µl/well. Coating overnight at 4° C. Blocking with PBS with 10% foetal calf serum (FCS) for 1 hour at room temperature. Between all subsequent steps, immunoplates were washed 5 times with PBS with 0.05% Tween 20.

Plate layout of samples: Tests for influenza IgG antibodies and IgG antibodies in general, were tested on the same immunoplate, as well as human IgG standards. All samples were tested in duplicate.

Test samples: Samples to be tested: LOH "serum" (1:3 dilution of plasma). Neat and 10-fold dilutions in PBS with 0.05% Tween 20 and 5% FCS (Diluent), 100 µl/well. IgG standard: Sigma 1-4506 (lot 96H8840): 10 µg IgG/ml, 10-fold dilutions in PBS with 0.05% Tween20 and 5% FCS, 100 µl/well.

Final cell pellet of 300 µl was in a PBS solution containing 1:9,368 dilution of serum. To this pellet was added 700 µl PBS (=1:3.33 dilution). Final pellet had $2.0 \times 10^7$ cells and contained a serum contamination of 1:31,200. Final supernatant tested was equivalent to 1:9,370 dilution of serum.

Cell lysates: Lysates were adjusted to be equivalent to 800,000, 200,000 and 50,000 cells/well, 100 µl/well.

TABLE 1

Cell lysate mixtures for testing

| Cell number/well | µl cell pellet | µl DISRUPTION BUFFER | µl Diluent | SUM µl | Dilution relative final cell wash |
|---|---|---|---|---|---|
| 800,000 | 240 | 240 | 126 | 606 | 1:(2.53 × 3.33) |
| 200,000 | 60 | 60 | 486 | 606 | 1:(10.1 × 3.33) |
| 50,000 | 15 | 15 | 576 | 606 | 1:(40.4 × 3.33) |

Contamination by serum antibodies, relative the final cell wash, of cell preparations were calculated to be:

1:8.4 (10.6%) for 800,000 cells

1:33.7 (2.9%) for 200,000 cells, and

1:134.8 (0.7%) for 50,000 cells.

All antibody samples were incubated for 90 minutes at room temperature.

Secondary antibody: Biotin-labelled goat anti-human IgG (γ-chain specific), Sigma B-1140 (lot 96H8886), used at 1:500 in PBS with 0.05% Tween20 and 5% FCS, 100 µl/well. Incubated for 60 minutes at room temperature.

Conjugate: ExtrAvidin peroxidase conjugate, Sigma E-2886 (lot 28H4824) diluted 1:1000 in PBS with 0.05% Tween20 and 5% FCS, 100 µl/well. Incubated for 60 minutes at room temperature.

Development: Substrate tablets (o-Penylene diamine dihydrochloride), Sigma P-8287 (lot 88H8250). One tablet (10 mg) was dissolved in 25 ml 0.1M phosphate-citrate buffer, pH 5.0, and supplemented with 20 µl perhydrol (30% $H_2O_2$). 100 µl/well of substrate solution was added, and the reaction was arrested after 10 minutes with 50 µl/well of 1M $H_2SO_4$. Optical density was read at 492 nm in a Titertek Multiskan PLUS reader (Flow Laboratories).

Results

Estimation of quantities of IgG was based on interpolation from standard curve obtained from the dilutions of the IgG standard. All test samples were tested in duplicate and mean of optical density readings were used for subsequent calculations.

TABLE 2

Serum IgG antibodies

| Antibodies | Serum antibodies (µg/ml) | % |
|---|---|---|
| IgO general | 2,365 | 100.0 |
| Influenza B | 70 | 3.0 |
| Influenza A | 112 | 4.8 |

TABLE 3

Release of IgG antibodies from disrupted lymphocytes

| Specificity | Number of lymph-ocytes in 100 µl well ($10^3$) | IgG de-tected in well (ng) | Serum IgG contamination of cells (ng) | Net IgG from each lympho-cytes in well (ng) | Net IgG from each lymphocyte ($10^{-6}$ ng) |
|---|---|---|---|---|---|
| Influenza A | 50 | 1.06 | 0.338/134.8 = $2.5 \times 10^{-3}$ | 1.06 | 2.12 |
|  | 200 | 10.72 | 0.336/33.7 = $10. \times 10^{-3}$ | 10.71 | S.35 |
| Influenza B | 200 | 0.38 | Below detection | 0.38 | 0.19 |
|  | 800 | 1.29 | Below detection | 1.29 | 0.16 |
| IgG general | 50 | 13.29 | 10.6/134.8 = 0.08 | 13.21 | 26.42 |
|  | 200 | 44.6 | 10.6/33.7 = 0.32 | 44.28 | 22.14 |

TABLE 4

SUMMARY: IgG detection in peripheral blood lymphocytes and serum

| Antibody Specificity | Net IgG from lymphocytes in each well ($10^{-5}$ ng) | % | Serium IgG µg/ml | % |
|---|---|---|---|---|
| Influenza A | 3.74 | 15.4 | 112 | 4.8 |
| Influenza B | 0.18 | 0.7 | 70 | 3.0 |
| IgG general | 24.28 | 100.0 | 2,365 | 100.0 |

CONCLUSION: Subject LOH was infected with influenza A virus, as can be clearly seen from Table 3. Using these data one can assume that 100,000 lymphocytes/well should give approximately 20 ng/ml of influenza A IgG antibodies, in contrast to approximately 2 ng/ml for influenza B antibodies. The former concentration of cells will for practical purposes give an ELISA signal for influenza A specific antibodies that can be conveniently measured, but not for influenza B antibodies. This is in contrast to the levels of influenza antibodies measured in serum (Table 2), where the levels of influenza A and B antibodies are very similar. Such serum antibodies would most likely be preexisting cross-reactive antibodies from previous exposures. IC has been known and demonstrated for many years that influenza memory can be reactivated through subsequent exposures with heterologous viruses, the so-called "antigenic sin", most probably through a local "bystander" effect in the lymphoid tissue where the initial immune processing takes place.

The reasons why antibodies from disrupted lymphocytes in our test also gave a measurable, albeit small, ELISA signal with the influenza B antigen, i.e. not the offending virus for subject LOH, could be a consequence of such non-specific reactivation of memory lymphocytes as a consequence of the immune assault by the influenza A virus. However, this unusual reactivation of memory cells is believed to be an influenza related phenomenon and will not be relevant for other infectious agents. Thus, it must be expected that an even clearer distinction between the signals given for antigens from the infectious agent in question and other agents will be observed.

The current method requires about 100 µl heparinized blood (equals 100,000 lymphocytes) for each antigen specific antibody to be tested for, allowing the use of capillary blood samples to be used.

Example 2

Kinetics

This is a clinical influenza vaccine trial. Nine healthy subjects: 6 females aged 24-27 years (mean 26.2) and 3 males aged 24-31 years (mean 28.3) were enrolled. They were informed by the doctor in charge of the relevant contraindications for vaccination, and all of them informed the doctor that they did not know of any such contraindications. None had been vaccinated against influenza previously. All vaccines completed the trial and allowed peripheral blood samples to be drawn as described below. Subjects were given licensed trivalent inactivated whole virus vaccine (Vaxigrip) containing A/Sydney/5/97($H_3N_2$)-like virus containing 15 µg haemagglutinin/dose A/Beijing/262/95(H1N1)-like virus containing 15 µg haemagglutinin/dose B/Beijing/184/93-like virus containing 15 µg haemagglutinin/dose from Mériex Sérums & Vaccines (France)

Heparinized blood samples were taken as described under Example 1. All procedures were as described under Example 1, except that lymphocytes were disrupted by freezing/thawing (twice) by inserting lymphocyte vials into liquid N2 and holding under running tap water.

Additionally a haemagglutination-inhibition (HI) test were done with receptor-destroying enzyme treated plasma samples according to standard procedures Kendal et al., 1982, in "Concepts and Procedures for Laboratory-Based Influenza Surveillance", Viral Disease Unit, WHO, Geneva using 4 haemagglutination units of the A/Nanchang virus and 0.7% turkey erythrocytes. Plasma were tested in twofold dilution steps and titres were scored as the reciprocal of highest dilution giving complete inhibition of virus haemagglutination. Samples obtained at day of vaccination, after 7 days and after 13 days were used.

Results

FIG. 1 shows the amount (in ng) of IgG against surface antigens from the related A/Nanchang/933/95(H3N2) (see Example 1) using solutions obtained from 300K disrupted lymphocytes for each of the nine vaccinated subjects (bars). They are ranged according to the quantity of influenza specific IgG antibodies obtained from the disrupted lymphocytes. The left-hand scale for ng IgG is not the same for all the subjects. Superimposed is shown HI titres (dotted line) against the A/Nanchang virus. A titre of 40 is by international consensus considered to be protective.

Conclusion

Classically, the HI antibodies are considered to be the "golden standard" influenza antibodies, together with virus neutralizing antibodies. HI titres 40 are considered to be protective according to international consensus. FIG. 1 shows that four of the nine subjects (persons 2, 5-7) obtained such antibodies at day 7, and all subjects, except persons 3 and 10, had such HI titres on day 13. For all subjects there were high levels of influenza specific IgG detected in disrupted lymphocytes already on day 7, and for five subjects (persons 3, 4, 8-10) only antibodies from disrupted lymphocytes, and not protective HI antibody levels, were detected on day 7.

Furthermore, the specificity of influenza IgG antibodies were evident by the appearance of such antibodies on day 7 and the disappearance of the same antibodies on day 13, since on day 13 most subjects had significant levels of serum antibodies.

Example 2 clearly emphasizes that the detected antibodies from disrupted lymphocytes were not contaminated by serum antibodies trapped in the lymphocyte pellet, as was also clearly demonstrated in Example 1.

Example 3

Simplified Method for Purifying Lymphocytes from Serum! Plasma Contaminants

Typically, lymphocytes sufficiently free from contaminating serum/plasma antibodies can be separated through three successive centrifugation steps. 300 µl whole blood is mixed with 10 ml diluent consisting of 2 parts PBS and 1 part distilled water. The mixture is centrifuged for 2020 minutes at room temperature at 400×g. The supernatant is discarded and to the pellet is added 10 ml PBS. The suspension is centrifuged as above, and the cycle is repeated once. The final pellet, suspended in 100 µl PBS, is used as lymphocyte source for subsequent assays.

Example 4

Storage of Blood Before Lymphocyte Purification

Male subject (EJAa, 20 years) was given licensed inactivated trivalent influenza vaccine according to the manufacturer s instructions (see Example 2). Five ml of heparinized blood samples were taken at day of vaccination (Day 0) and on Day 9 after vaccination. Immediately after collection 300 µl blood were subjected to three washing/centrifugation cycles as described above under Example 3, and lymphocytes were disrupted as described under Example 1. The retaining blood sample was stored at 4° C. for 4 days, followed by storage at room temperature for 4 hours before a new round of lymphocyte purification was initiated. All subsequent ELISA tests were performed as described as under Example 1. Haemagglutination-inhibition tests (HI) were done with the homologous vaccine strains as described in Example 2.

TABLE 5

Storage of blood at 40 C. for 4 days, followed by 4 hours at room temperature.
Effect on antibody activity from disrupted lymphocytes

| Days after vaccination | | H3N2 | | H1N | | B | |
|---|---|---|---|---|---|---|---|
| | | Immediate | After 4 days | Immediate | After 4 days | Immediate | After 4 days |
| Day 0 | HI | 640 | | <10 | | <10 | |
| | Cells | 704 | 598 | 058 | 060 | 224 | 210 |
| Day 9 | HI | 640 | | 20 | | 40 | |
| | Cells | 811 | 901 | 091 | 100 | 446 | 446 |

All entries are Optical Density at 492 nm×1000 and HI titres of plasma antibodies. "Cells" are antibodies from disrupted lymphocytes obtained from 100 µl blood.

Results

This subject had already been found to have significant HI titres against the A/Sydney/5/97(H3H2) vaccine component before vaccination, and the released antibodies from lymphocytes did not increase significantly from day 0 to day 9, nor did the HI titre. The HI vaccine response to the H1N1 component A/Beijing/262/95 was poor, and this was also seen for the cell assay. The most clearly seen response was against the influenza B component B/Beijing/184/93, where HI titres rose from <10 to 40. This was mirrored also for the cell assay.

Leaving the blood at 4° C. for 4 days, followed by 4 hours at room temperature, did not affect the recorded antibody activity from disrupted lymphocytes. The immediate results and those obtained after storage for four days did not vary to any significant extent.

Other experiments have also shown that even after six days under similar storage conditions (refrigeration, interrupted by 6 hours at room temperature) did not affect the ensuing measurement of antibodies from disrupted lymphocytes.

The invention claimed is:

1. A method of determining whether newly synthesized target antibody is present in a body fluid sample in response to an immunogen comprising:
   (i) lysing lymphocytes to release said target antibodies or parts thereof from said lymphocytes, wherein said lymphocytes are obtained from a whole blood sample containing lymphocytes from a subject suspected of undergoing an immune response whereby the lymphocytes are in acute phase of antibody synthesis; and
   (ii) detecting said released target antibodies or parts thereof from the lysed lymphocytes, whereby the presence of newly synthesized target antibody from the lymphocytes indicates whether newly synthesized antibodies are in the body fluid sample.

2. The method of claim 1, wherein said blood sample is peripheral blood.

3. The method as claim 1, wherein the sample is not incubated to promote synthesis and/or secretion of antibodies prior to the method.

4. The method as claimed in claim 1, wherein the lymphocytes are lysed by using physical disruption means or cell-disrupting buffers or solutions.

5. The method as claimed in claim 1, wherein the target antibodies or parts thereof are detected by binding to one or more antigens which recognize said antibodies or parts thereof.

6. The method as claimed in claim 1, wherein the released target antibodies are detected by means of a solid phase binding assay.

7. The method of claim 6, wherein the solid phase of said solid phase binding assay carries one or more antigens recognized by the target antibody or antibodies or parts thereof to be detected.

8. The method of claim 6, wherein the solid phase of said solid phase binding assay carries one or more antibodies, which recognize the target antibody or target antibodies or parts thereof to be detected.

9. The method of claim 8, wherein one or more antigens, recognized by the target antibodies immobilized on said solid phase, are contacted with said solid phase.

10. The method of claim 7 or 8, wherein one or more antibodies, which recognize target antibodies immobilized on said solid phase, are contacted with said solid phase.

11. The method of claim 6, wherein multiple solid phases are employed each bearing a different target antigen, which recognizes a different target antibody.

12. The method as claimed in claim 1, wherein the method is performed on neonate or infant blood samples for distinguishing between newly synthesized antibodies and passively transferred maternal antibodies.

13. The method as claimed in claim 1, wherein prior to disrupting the lymphocytes, or after disruption but prior to the detection step, said sample is stored at about 4° C. or less.

14. The method as claimed in claim 1, wherein said blood sample for preparing lymphocytes for use in the method, has a volume of less than 1 ml.

15. The method as claimed in claim 1, wherein the lymphocytes are directly isolated from said blood sample.

16. The method as claimed in claim 1, wherein the detecting step is performed by immunoassay.

17. The method of claim 16, wherein the immunoassay is enzyme linked immunosorbent assay.

18. The method as claimed in claim 1, wherein the detection step comprises the addition of an enzyme-antibody conjugate or an enzyme-antigen conjugate, and the addition of a soluble substrate, wherein said soluble substrate yields a spectrophotometrically detectable signal.

19. The method as claimed in claim 1, wherein the target antibodies or parts thereof are detected by binding to one or more antigens which recognize said antibodies or parts thereof and wherein said method is additionally performed using a negative control antigen.

20. The method of claim 1 further comprising determining the amount of a newly synthesized target antibody comprising:
   comparing said antibody binding to antibody binding in control and/or reference samples, whereby to obtain a determination of the amount of newly synthesized antibody in response to said immunogen.

21. The method as claimed in claim 1 or 20, wherein the newly synthesized antibody is synthesized in vivo.

22. The method as claimed in claim 1 or 20, wherein the newly synthesized antibody is an antigenically active antibody, which has been produced or synthesized by and within a lymphocyte in vivo as part of an ongoing immune response.

* * * * *